United States Patent
Li et al.

(10) Patent No.: US 10,662,142 B2
(45) Date of Patent: May 26, 2020

(54) PROCESS FOR PRODUCTION OF AROMATIC COMPOUNDS COMPRISING AT LEAST TWO AMINE FUNCTIONS

(71) Applicants: RHODIA OPERATIONS, Paris (FR); LANZHOU INSTITUTE OF CHEMICAL PHYSICS, CHINESE ACADEMY OF SCIENCE, Lanzhou, Gansu Province (CN)

(72) Inventors: Peng Li, Shanghai (CN); Armin T. Liebens, Nancy (FR); Feng Shi, Gansu Province (CN); Hangkong Yuan, Lanzhou (CN)

(73) Assignees: RHODIA OPERATIONS, Paris (FR); LANZHOU INSTITUTE OF CHEMICAL PHYSICS, CHINESE ACADEMY OF SCIENCE, Lanzhou, Gasnu Province (CN)

( * ) Notice: Subject to any disclaimer, the term of this patent is extended or adjusted under 35 U.S.C. 154(b) by 0 days.

(21) Appl. No.: 16/347,967

(22) PCT Filed: Nov. 6, 2017

(86) PCT No.: PCT/CN2017/109477
§ 371 (c)(1),
(2) Date: May 7, 2019

(87) PCT Pub. No.: WO2018/086491
PCT Pub. Date: May 17, 2018

(65) Prior Publication Data
US 2019/0292128 A1    Sep. 26, 2019

(30) Foreign Application Priority Data
Nov. 9, 2016 (WO) ................ PCT/CN2016/000622

(51) Int. Cl.
| | | |
|---|---|---|
| *C07D 307/02* | (2006.01) | |
| *C07C 209/78* | (2006.01) | |
| *B01J 23/755* | (2006.01) | |
| *B01J 37/02* | (2006.01) | |
| *B01J 37/03* | (2006.01) | |
| *B01J 37/04* | (2006.01) | |
| *B01J 37/08* | (2006.01) | |
| *B01J 37/18* | (2006.01) | |
| *B01J 25/02* | (2006.01) | |
| *C07D 307/52* | (2006.01) | |
| *B01J 21/04* | (2006.01) | |
| *B01J 23/40* | (2006.01) | |

(52) U.S. Cl.
CPC .............. *C07C 209/78* (2013.01); *B01J 21/04* (2013.01); *B01J 23/755* (2013.01); *B01J 25/02* (2013.01); *B01J 37/0236* (2013.01); *B01J 37/031* (2013.01); *B01J 37/04* (2013.01); *B01J 37/08* (2013.01); *B01J 37/088* (2013.01); *B01J 37/18* (2013.01); *C07D 307/52* (2013.01); *B01J 23/40* (2013.01)

(58) Field of Classification Search
CPC ......... C07C 209/78; B01J 37/04; B01J 37/18; B01J 37/08; B01J 37/031; B01J 37/0236; B01J 23/755; C07D 307/02
USPC .......................................................... 549/492
See application file for complete search history.

(56) References Cited

U.S. PATENT DOCUMENTS

| | | | |
|---|---|---|---|
| 2,989,546 | A | 6/1961 | Garber et al. |
| 2,995,582 | A | 8/1961 | Garber et al. |
| 4,152,353 | A | 5/1979 | Habermann |
| 4,409,399 | A | 10/1983 | Swift et al. |
| 4,912,260 | A | 3/1990 | Dobson et al. |
| 5,530,127 | A | 6/1996 | Reif et al. |
| 2003/0139289 | A1 | 7/2003 | Renken et al. |

FOREIGN PATENT DOCUMENTS

| | | |
|---|---|---|
| CN | 1138499 A | 12/1996 |
| CN | 104277017 A | 1/2015 |
| CN | 104277018 A | 1/2015 |
| CN | 105593220 A | 5/2016 |
| CN | 107011194 A | 8/2017 |
| EP | 0312253 A2 | 4/1989 |
| WO | 9009368 A1 | 8/1990 |
| WO | 03051508 A1 | 6/2003 |
| WO | 2014059574 A1 | 4/2014 |
| WO | 2014198057 A1 | 12/2014 |
| WO | 2015054828 A1 | 4/2015 |
| WO | 2016004867 A1 | 1/2016 |

OTHER PUBLICATIONS

Pera-Titus et al., "Catalytic Amination of Biomass-Based Alcohols", ChemSusChem 2014, vol. 7, pp. 720-722.
Guillena et. al., "Hydrogen Autotransfer in the N-Alkylation of Amines and Related Compounds using Alcohols and Amines as Electrophiles", Chem. Rev. 2010, vol. 110, No. 3, pp. 1611-1641.

*Primary Examiner* — Taylor V Oh

(57) ABSTRACT

Provided is a process for the production of an aromatic compound comprising at least two amine functions, comprising reacting an aromatic compound having at least one hydroxyl function and at least one aldehyde function with a second reactant having an amine function, in the presence of a reductant agent and a catalyst comprising at least one metal element in elemental form and/or at least one metal oxide.

14 Claims, No Drawings

PROCESS FOR PRODUCTION OF AROMATIC COMPOUNDS COMPRISING AT LEAST TWO AMINE FUNCTIONS

CROSS-REFERENCE TO RELATED APPLICATION

This application is a U.S. national stage entry under 35 U.S.C. § 371 of International Application No. PCT/CN2017/109477 filed Nov. 6, 2017, which claims priority to International Patent Application No. PCT/CN2016/000622 filed on Nov. 9, 2016. The entire contents of these applications are explicitly incorporated herein by this reference.

TECHNICAL FIELD

The present invention concerns a process for the production of an aromatic compound comprising at least two amine functions, comprising reacting an aromatic compound having at least one hydroxyl function and at least one aldehyde function with a second reactant having an amine function, in the presence of a reductant agent and a catalyst comprising at least one metal element in elemental form and/or at least one metal oxide.

PRIOR ART

Amines are of significant importance for the chemical industry, but also for numerous biological processes. For instance, amino acids and nucleotides constitute essential biological building blocks and numerous bioactive compounds such as vitamins, hormones, alkaloids, neurotransmitters, or natural toxics contain amino groups. It is, therefore, not surprising, that numerous amines and their derivatives find application as agrochemicals, pharmaceuticals, or food additives. Several million tons of amines are produced annually. They are widely used in both the bulk and fine chemical industries as fundamental materials, additives, dyes, and agrochemicals.

Diamines are used as monomers to prepare polyamides, polyimides and polyureas. Recently, there are lots of researches focusing on aromatic compounds comprising amine functions, especially furanic compounds comprising two amine functions.

CN 104277018A discloses a method for preparing 2,5-bis(aminomethyl)furan (BAMF) by catalytic reductive amination of 2,5-diformyl furan (DFF). According to this method, ammonia is used as an amine source, hydrogen is used as a hydrogen source and a supported metal is used as a catalyst. The metal catalyst consists of active metal component(M), which is selected from a group consisting of Ni, Cu, Co, Cr, Sn, Al, Bi, Ce, Pt, Pd, Au, Ag, Rh, Ru, Ir, Re and any combination thereof and metal oxide ($M_xO_y$) support, which is selected from a group consisting of CaO, MgO, $La_2O_3$, $Y_2O_3$, $CeO_2$, $ZrO_2$, $Al_2O_3$, $TiO_2$, $Nb_2O_5$, $SnO_2$, $V_2O_5$, $MnO_2$, $Fe_2O_3$, $Fe_3O_4$, $MoO_3$ and any combination thereof. The starting reactant DFF is normally prepared from a biomass-derived compound 5-hydroxymethylfurfural (HMF).

WO2014/198057 teaches a process for the production of furanic compound comprising at least one amine function, comprising reacting a furanic compound having at least one hydroxyl function or at least one aldehyde function with a second reactant having an amine function, in the presence of an iridium catalyst. Wherein, HMF was converted to the corresponding diamine in one pot by reacting with an amine and an external reductant. Disadvantageously, homogeneous catalyst is more difficult to be recycled and reused than heterogeneous catalyst.

Thus, the reported prior arts are still not ideal due to high production cost of raw materials and difficulties in industrial operation.

It exists then a need to provide a process for producing aromatic compounds comprising at least two amine functions by direct amination of economical starting reactant in the presence of a heterogeneous catalyst with high conversion, sufficient yield and selectivity, notably permitting then to produce aromatic compounds comprising amine functions by shifting from conventional petrochemical feedstocks towards biomass-based feedstocks as the furanic compounds, 5-hydroxymethylfurfural (HMF) for instance.

INVENTION

It appears now that it is perfectly possible to carry out a process for producing aromatic compounds comprising at least two amine functions by direct amination of economical starting reactant in the presence of a heterogeneous catalyst, to notably obtain sufficient yield and conversion in comparison with the process reported in the prior arts.

The present invention then concerns a process for the production of an aromatic compound comprising at least two amine functions, comprising reacting:

A first reactant being an aromatic compound having at least one hydroxyl function and at least one aldehyde function, with A second reactant being a compound of formula (I),

$$R-NH_2 \quad\quad (I)$$

in the presence of a catalyst and a reductant agent,
wherein:
The catalyst comprises at least one metal element in elemental form and/or at least one metal oxide,
R is H or a hydrocarbon group.

Other characteristics, details and advantages of the invention will emerge even more fully upon reading the description which follows.

DEFINITIONS

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The term "and/or" includes the meanings "and", "or" and also all the other possible combinations of the elements connected to this term.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to", "including" and "including but not limited to" are used interchangeably.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a temperature range of about 120° C. to about 150° C. should be interpreted to include not only the explicitly recited limits of about 120° C. to about 150° C., but also to include sub-ranges, such as 125° C. to 145° C., 130° C. to 150° C., and so forth, as well as individual amounts, including fractional amounts, within the specified ranges, such as 122.2° C., 140.6° C., and 141.3° C., for example.

The term "between" should be understood as being inclusive of the limits.

It is specified that, in the continuation of the description, unless otherwise indicated, the values at the limits are included in the ranges of values which are given. It should be noted that in specifying any range of concentration, any particular upper concentration can be associated with any particular lower concentration.

As used herein, the terminology "($C_n$-$C_m$)" in reference to an organic group, wherein n and m are each integers, indicates that the group may contain from n carbon atoms to m carbon atoms per group.

"Alkyl" as used herein means a straight chain or branched saturated aliphatic hydrocarbon. Preferably alkyl group comprises 1-18 carbon atoms. Representative saturated straight chain alkyls include methyl, ethyl, n-propyl, n-butyl, n-pentyl, and the like; while saturated branched alkyls include isopropyl, sec-butyl, isobutyl, tert-butyl, isopentyl, and the like.

"Alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbon atoms of the alkenyl group. Representative unsaturated straight chain alkenyls include ethenyl, propenyl, butenyl, pentenyl, hexenyl, heptenyl, octenyl, nonenyl, decenyl and the like.

The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups.

"Aryl" as used herein means a 6-carbons monocyclic or 10-carbons bicyclic aromatic ring system wherein 0, 1, 2, 3, or 4 atoms of each ring are substituted. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

"Cycloalkyl" as used herein means cycloalkyl groups containing from 3 to 8 carbon atoms, such as for example cyclohexyl.

"Heterocyclic" as used herein means heterocyclic groups containing up to 6 carbon atoms together with 1 or 2 heteroatoms which are usually selected from O, N and S, such as for example radicals of: oxirane, oxirene, oxetane, oxete, oxetium, oxalane (tetrahydrofurane), oxole, furane, oxane, pyrane, dioxine, pyranium, oxepane, oxepine, oxocane, oxocinc groups, aziridine, azirine, azirene, azetidine, azetine, azete, azolidine, azoline, azole, azinane, tetrahydropyridine, tetrahydrotetrazine, dihydroazine, azine, azepane, azepine, azocane, dihydroazocine, azocinic groups and thiirane, thiirene, thiethane, thiirene, thietane, thiete, thietium, thiolane, thiole, thiophene, thiane, thiopyrane, thiine, thiinium, thiepane, thiepine, thiocane, thiocinic groups.

"Heterocyclic" may also mean a heterocyclic group fused with a benzene-ring wherein the fused rings contain carbon atoms together with 1 or 2 heteroatom's which are selected from N, O and S.

As used herein, the term "Lanthanides" refer to metals with atomic number 57 to 71.

As used herein, the term "Actinides" refer to the metals with the atomic number 89 to 103.

Should the disclosure of any patents, patent applications, and publications which are incorporated herein by reference conflict with the description of the present application to the extent that it may render a term unclear, the present description shall take precedence.

INVENTION

As used in the present invention, the term "aromatic compound having at least one hydroxyl function and at least one aldehyde function" refers to a compound having at least one aromatic ring substituted with at least one hydroxyl function and at least one aldehyde function.

The aromatic ring as used herein can be a hydrocarbon or heterocyclic ring, and may be chosen from the group consisting of benzene, pyrene, furan, thiophene, terthiophene, pyrrole, pyridine, terpyridine, pyridine oxide, pyrazine, indole, quinoline, purine, quinazoline, bipyridine, phenanthroline, naphthalene, tetralin, biphenyl, cyclohexylbenzene, indan, anthracene, phenanthrene, fluorene, and azulene, each being optionally substituted with at least one substitution chosen from the group consisting of $C_1$-$C_{24}$ alkyl, amino, hydroxyl, carboxyl, ester, cyano, nitro, halogen, and oxygen. Preferably, the aromatic ring could be chosen in the group consisting of substituted or unsubstituted furan, thiophene, benzene, pyrrole and pyridine.

Preferably, first reactant being an aromatic compound having at least one hydroxyl function and at least one aldehyde function of the invention may be an aromatic compound comprising one hydroxyl function and one aldehyde function.

First reactant may notably be chosen in the group consisting of: 5-hydroxymethyl furfural (HMF), 5-(3-(hydroxymethyl)phenyl)furfural, 5-(4-(hydroxymethyl)phenyl)furfural, 4-(hydroxymethyl)benzaldehyde, 3-(hydroxymethyl)benzaldehyde, 5-formyl-2-(hydroxymethyl)benzonitrile, 3-(5-(hydroxymethyl)furan-2-yl)acrylaldehyde and 5-(hydroxymethyl)thiophene-2-carbaldehyde, among which 5-hydroxymethyl furfural (HMF), 3-(hydroxymethyl)benzaldehyde or 5-formyl-2-(hydroxymethyl) benzonitrile is preferred.

HMF is a biomass-derived compound that can be applied to the synthesis of precursors of pharmaceuticals, furanose-based polymers, monomers of polymers such as polyamide, and other organic intermediates that can lead to numerous chemical products.

As previously expressed, second reactant is a compound of formula (I):

$$R—NH_2 \quad (I)$$

R may represent hydrogen, straight, branched or cyclic hydrocarbon group that can be an alkyl, alkenyl, aryl, cycloalkyl or heterocyclic group, eventually comprising one or several heteroatoms such as O, S, F, and N. Preferred groups for R may be for example: H, alkyl, phenyl, benzyl, cycloalkyl, and cycloalkane. R may comprise from 1 to 10 carbon atoms.

Preferred second reactants of the present invention, such as compounds of formula (I), may be chosen in the group consisting of: ammonia, methylamine, n-heptylamine, allylamine, benzylamine, 3-phenylprop-2-enylamine, cyclohexanamine, and (tetrahydrofuran-2-yl)methanamine.

Preferred second reactant may notably be ammonia. It should be understood by the people having ordinary in the art that ammonia or an ammonia-liberating compound or mixtures thereof should also been considered as second reactant of present invention. Examples of such ammonia-liberating compounds include urea, uric acid, ammonium salts and derivatives of a primary amide, for example, symmetrical and unsymmetrical carbamates, carbaminates, semicarbazides and semicarbazoles, or aminium salts or organic/inorganic esters thereof. Preference may be given to using ammonia itself, with liquid or gaseous ammonia being able to be used in this embodiment.

Molar ratio of second reactant to first reactant may be comprised from 5:1 to 300:1, preferably from 10:1 to 150:1 and more preferably from 20:1 to 120:1.

As the preferred molar ratio of ammonia, which may be formed from the ammonia introduced and/or the ammonia-liberating compound or the sum of such compounds used in the process to the equivalents of first reactant, a value in the range of 10:1-150:1 and preferably in the range of 20:1-120:1 may be set.

The reductant agent used in the process of the invention is also called reducing agent or reducer, herein refers to an organic or inorganic compound that donates a proton to another species, in a redox reaction. For instance in the reaction of the present invention, reductant agents donate protons to the transiently formed imines. Reductant agents used in the reaction may notably be hydrogen or a secondary alcohol, such as for example isopropanol, glycerol, 2-butanol, and cyclohexanol. Among them, hydrogen is preferable.

Molar ratio of the reductant agent to the first reactant may be comprised from 1:1 to 10:1, preferably from 1:1 to 5:1.

The aromatic compound comprising at least two amine functions are obtained at the end of the reaction. The compound may comprise at least two primary or secondary amine functions.

The aromatic compound comprising at least two amine functions obtained by the process of the present invention may preferably be chosen in the group consisting of: 2,5-bis(aminomethyl)furan, 5-(3-(aminomethyl)phenyl)furfurylamine, 5-(4-(aminomethyl)phenyl)furfurylamine, p-xylenediamine, m-xylenediamine, 2,5-bis(aminomethyl)benzonitrile, 1,2,4-triyltrimetanamine, 3-(5-(aminomethyl)furan-2-yl)allylamine and bis(aminomethyl)thiophene, among which 2,5-bis(aminomethyl)furan, m-xylenediamine, 2,5-bis(aminomethyl)benzonitrile or 1,2,4-triyltrimetanamine is preferred.

Preferred reactions of the present invention are the following:
Reaction of 5-hydroxymethyl furfural with ammonia to produce 2,5-bis(aminomethyl)furan.
Reaction of 3-(hydroxymethyl)benzaldehyde with ammonia to produce m-xylenediamine.
Reaction of 5-formyl-2-(hydroxymethyl)benzonitrile with ammonia to produce 2,5-bis(aminomethyl)benzonitrile and 1,2,4-triyltrimetanamine.

As previously expressed, the catalyst usable for the present process is a catalyst comprising at least one metal element in elemental form and/or at least one metal oxide.

Metal oxide compounds comprise typically at least one oxygen atom and at least one metal atom which is chemically bound to the oxygen atom; the electronegativity of the oxygen atom is obviously higher than the electronegativity of the metal atom.

Said metal oxide may comprise at least one metal element. Preferably, the metal oxide may comprise at least two metal elements. In one preferred embodiment, the metal oxide may comprise two or three metal elements.

In one embodiment, catalyst of present invention may comprise a support and at least one metal element in elemental form and/or at least one metal oxide, wherein the metal element in elemental form or metal element comprised in metal oxide could be chosen in the group consisting of: (i) elements of group IA, IIA, IIIA, IVA, VA, VIA and VIIA of the Periodic Table, (ii) elements of groups IB, IIB, IIIB, IVB, VB, VIB, VIIB and VIIIB of the Periodic Table, (iii) lanthanides, (iv) actinides, and (v) any combination thereof.

In present invention, hydrogen is not included in metal element chosen in Group IA of the Periodic Table. Carbon is not included in metal element chosen in Group IVA of the Periodic Table. Nitrogen and phosphorus are not included in metal element chosen in Group VA of the Periodic Table. Oxygen, sulfur and selenium are not included in metal element chosen in Group VIA of the Periodic Table.

Some of the elements encompassed by the description above and understood to be metals for the purpose of the present invention, are sometimes also referred to as metalloids. The term metalloid is generally designating an element which has properties between those of metals and non-metals. Typically, metalloids have a metallic appearance but are relatively brittle and have a moderate electrical conductivity. The six commonly recognized metalloids are boron, silicon, germanium, arsenic, antimony, and tellurium. Other elements also recognized as metalloids include aluminum, polonium, and astatine. On a standard periodic table all of these elements may be found in a diagonal region of the p-block, extending from boron at one end, to astatine at the other.

Preferably, catalyst of present invention may comprise a support and at least one metal element in elemental form and/or at least one metal oxide of at least one metal element, wherein the metal element in elemental form or metal element comprised in metal oxide could be chosen in the group consisting of: (i) elements of group IA, IIA, IIIA, IVA, VA, VIA and VIIA of the Periodic Table, (ii) elements of groups IB, IIB, IIIB, IVB, VB, VIB, VIIB and VIIIB of the Periodic Table, and (iii) any combination thereof. More preferably, the metal element in elemental form or metal element comprised in metal oxide could be notably chosen in the group consisting of metals, such as nickel, cobalt, tin, aluminum, chromium, platinum, palladium, rhodium, ruthenium, iridium, silver, gold, cerium, bismuth, rhenium and copper and most preferably chosen in the group consisting of nickel, cobalt, copper, tin, aluminum and chromium.

The support of catalyst may be chosen in the group consisting of Kieselguhr, silica, alumina, silica-alumina, clay, titania, zirconia, magnesia, calcia, lanthanum oxide, niobium oxide, carbon and any combination thereof.

The supported catalyst may have any shape such as powder, grains or pellets. The weight ratio of metal element in this embodiment may be comprised from 0.5 wt % to 80 wt % based on total weight of catalyst and preferably from 10 wt % to 70 wt % and more preferably rom 20 wt % to 60 wt %. Said metal element refers to metal comprised in elementary substance and/or oxides.

The supported catalyst includes those commercially available under the trade designations "PRICAT CU 60/35", "T-4419", "PRICAT Ni 52/35", "PRICAT Ni 62/15", "T-8031", "C18-HA", "PRICAT Ni 20/15", "T-4466", "T-4489", "HTC Ni 500", "Ni 1404 T3/16 RS", "Ni 5132 RS" (available from Johnson Matthey, Sud-Chemie or BASF).

In another embodiment, catalyst of present invention may comprise an oxide represented by the general formula (II), wherein:

$$M_aM'_bO_c \quad (II)$$

M represents one or more transition metal elements selected from a group consisting of Cu, Zn, Ti, Zr, Hf, Rh, Ir, Ni, Pd and Pt, preferably from a group consisting of Cu, Ni, and Pt;
M' represents one or more poor metal elements selected from a group consisting of Al, Ga, In, Sn, Pb, Tl, Bi, and Po, and is preferably Al;
a and b independently represent a number from 0.01 to 10; and
c is greater than zero and less than a number sufficient to satisfy the valence requirements of the other elements present when in a fully oxidized state.

When in use for the present invention, the oxide of formula (II) is in a reduced state, thus containing less oxygen than necessary to satisfy the valence requirements of the metals present if in a fully oxidized state, as reflected in the definition of c in the formula (II).

In the preferred embodiments of formula (II), M represents Ni and/or Cu, M' represents Al, and the following formula (III) is complied, wherein:

$$Ni_wCu_xAl_yO_z \quad (III)$$

w or x is a number ranging from 0 to 3, preferably from 0 to 1; when w is 0, x is greater than 0 and when x is 0, w is greater than 0;
y is a number ranging from 0.1 to 2.5, preferably from 0.5 to 1.5; and
z is greater than zero and less than a number sufficient to satisfy the valence requirements of the other elements present when in a fully oxidized state.

In one preferred embodiment of formula (III), w and x are around 1, y is around 1.3, and z is larger than 2. In another preferred embodiment of formula (III), w is around 1, x is zero, y is around 1.3, and z is larger than 2.

The applicant also found that, in addition to the oxides of formula (II), catalyst may further comprise at least one noble metal component, to enhance its catalytic activity. Specifically, the noble metal is preferably loaded onto a surface of the oxide of formula (II), by doping or other conventional deposition means known in the art. Preferably, said noble metal is selected from Ru, Pt, and Pd.

The amount of noble metal, when used in combination with the oxide of formula (II) in the catalyst, is from 0.1 to 10 wt %, preferably from 0.1 to 8 wt %, and more preferably from 0.1 to 5 wt % based on the weight of said oxide of formula (II).

In one particularly preferred embodiment of the above category, the catalytically active portion of catalyst is essentially composed of a noble metal of Pd, Ru, or Pt and an oxide of formula (III), wherein w is around 1, x is zero or around 1, y is around 1.3, and z is larger than 2.

Catalyst comprising oxide of formula (II) might be produced by a "co-precipitation" method. As use herein, "co-precipitation" refers to a method: A mixture containing two or more metal ions is reacted with a precipitating agent, and a precipitate containing several metal components is formed.

The co-precipitation method to prepare the catalyst comprising oxide of formula (II) normally comprises the following steps:
(i) preparation of a mixture comprising the metal elements of the catalyst in ionic form;
(ii) adding a co-precipitating agent to the mixture to precipitate the metal elements of the catalyst, and obtain a slurry;
(iii) filtering, drying and thermally treating the slurry, to obtain a catalyst precursor; and
(iv) subjecting the catalyst precursor to reduction, to obtain the catalyst.

In a preferred embodiment, the co-precipitation method to prepare the catalyst comprising oxide of formula (II) comprises the following steps:
(i) preparation of a mixture comprising the metal elements of the catalyst in ionic form;
(ii) adding a co-precipitating agent to the mixture to precipitate the metal elements of the catalyst, and obtain a slurry;
(iii) filtering and drying the slurry, to obtain a catalyst precursor; and
(iv) subjecting the catalyst precursor to reduction, to obtain the catalyst.

Typically, step (i) comprises dissolving more than one metal salts in a solvent, e.g. water.

As the material used for co-precipitating agent in step (ii), basic solutions such as sodium carbonate, sodium bicarbonate, ammonium carbonate, ammonium bicarbonate, and ammonia water can be selected.

Optionally, the co-precipitating agent in step (ii) can be a combination of carbonate and alkali metal hydroxide. Preferred carbonate can be sodium carbonate, potassium carbonate or ammonium carbonate. Preferred alkali metal hydroxide can be sodium hydroxide or potassium hydroxide.

With regard to the thermal treatment means in step (iii), calcination is preferably used. The calcination is typically carried out at temperatures in a range of 350° C. to 750° C., and preferably from 450° C. to 600° C., and under any suitable gas atmosphere, e.g. in the presence of hydrogen, nitrogen, helium, argon and/or steam or mixtures thereof.

Conveniently, the reduction step (iv) may be performed by contacting the catalyst precursor with hydrogen. Hydrogen is normally present as a gas at low to moderate pressure in contact with the catalyst precursor. Partial pressures of hydrogen of at least one atmosphere are preferred. The reduction temperature in step (iv) is suitably between 200° C. and 600° C., preferably between 300° C. and 500° C.

Preferred examples of catalyst comprising oxide of formula (II) produced by "co-precipitation" method are NiAlO$_c$, CuNiO$_c$, CuNiAlO$_c$, CuNiMgO$_c$, RuCuNiAlO$_c$, CuNiZnO$_c$, PtNiZnO$_c$, CuZrO$_c$, wherein c has the same meaning as above defined.

In still another embodiment, the catalyst of present invention could even be selected from Raney catalysts such as Raney nickel, Raney cobalt and Raney copper.

Raney nickel is an alloy containing catalytically active nickel and a catalytically inactive component, such as aluminum or silicon. The Raney nickel alloy always has a very high surface area and also contains hydrogen gas (H$_2$) adsorbed on the nickel surface.

Weight ratio of catalyst to first reactant of present invention may be comprised from 1:20 to 2:1, preferably from 1:10 to 7:10.

The progress of the reaction towards the aromatic compounds comprising at least two amine functions may be followed using an appropriate method such as thin layer chromatography, nuclear magnetic resonance, high-pressure liquid chromatography, gas chromatography or a combination of the foregoing methods. Exemplary reaction times are 1 to 30 hours, preferably 10 to 25 hours.

The reaction temperature of present invention may be comprised from 20° C. to 200° C. and preferably from 100° C. to 150° C.

Preferably, the reaction medium heated to desired temperature by Gradient Temperature-elevating Method. For example, the reaction mixture could be premixed for 4 hours at room temperature and then heated for 16 hours at 150° C. to get complete reaction.

The reaction may be carried out in liquid or gas phase. Preferably, the reaction of the present process could be carried out in a liquid phase using a solvent. The solvent used should be liquid under the temperature and pressure throughout the reaction, and substantially inert to the reactants and products in the reaction mixture of the present process. Suitable examples of such solvent include: alcoholic solvent such as methanol, ethanol, 2-propanol, 1-butanol, isoamyl alcohol and n-octyl alcohol; an aromatic hydrocarbon solvent such as toluene; or an ether solvent such as methyl t-butyl ether, tetrahydrofuran and 1,4-dioxane, among which methanol, ethanol and 1,4-dioxane are preferred.

These solvents may be used in any amount with no specific restrictions, but desirably in an amount ranging from 0.5 to 50 times the weight of the first reactant used, and more preferably in an amount of 2 to 10 times the weight of the first reactant used.

The reactants, with an optional solvent, and the catalyst are typically combined in a reaction vessel and stirred to constitute the reaction mixture. The reaction mixture is typically maintained at the desired reaction temperature under stirring for a time sufficient to form the aromatic compounds comprising at least two amine functions, in the desired quantity and yield.

Although not specifically limited, the reaction of the present process is desirably carried out under a hydrogen partial pressure in a range of 0.1 to 25 MPa, and more preferably in a range of 0.5 to 20 MPa. Optionally, hydrogen may be added during the reaction to make up for the consumption or continuously circulated through the reaction zone.

The reaction may be carried out in the presence of air but preferably with an inert atmosphere such as $N_2$ or Ar.

The catalyst is typically removed from the reaction mixture using any solid/liquid separation technique such as filtration, centrifugation, and the like or a combination of separation methods. The product may be isolated using standard isolation techniques, such as distillation.

Preferably, at least part of the catalyst used in the process of the invention may be recycled. More preferably, all the catalyst is recycled to a fresh reaction solution.

Preferably, the recycled catalyst may be directly reused after physical separation from reaction solution.

Having generally described the invention, a further understanding may be obtained by reference to the examples below, which are provided for the sole purpose of illustration and not intending to limit the invention. Should the disclosure of any patents, patent applications, and publications which are incorporated herein by reference conflict with the description of the present application to the extent that it may render a term unclear, the present description shall take precedence.

EXPERIMENTAL PART

EXAMPLE 1

Preparation of Cu—Ni—Al Oxide Catalyst by Co-Precipitation

The solution of precipitant (9 g $Na_2CO_3$ dissolved into 60 mL of deionized water) was added to the solution of metal nitrites (1.44 g $Cu(NO_3)_2.3H_2O$, 3.48 g $Ni(NO_3)_2.6H_2O$ and 6.0 g $Al(NO_3)_3.9H_2O$, dissolved in 150 mL of deionized water) under stirring at 80° C. The obtained mixture was stirred for another 5 h, followed by drying at 100° C. for 2 hours and calcination at 400° C. for 4 hours.

The catalysts were pre-reduced before use —$H_2$ flow: 10 ml/min, $N_2$ flow: 30 ml/min, heated from room temperature to 500° C., ramp: 5° C./min, maintained at 500° C. for 40 min and cooled down.

EXAMPLE 2

Heterogeneously Catalytic Process Using Cu—Ni—Al Oxide Catalyst

To a 30 mL autoclave containing 0.5 mmol HMF, 60 mg CuNiAl oxide catalyst of Example 1 was introduced with 3 mL dioxane. The autoclave was purged with 3×5 bar hydrogen and the pressure was maintained at 1 bar finally. And then 0.23 g ammonia was introduced into the reactor. The reaction mixture was stirred at 150° C. for 16hours. Characterization by gas chromatography indicated 40% yield of 2,5-bis(aminomethyl)furan (BAMF) and 31% yield of 5-hydroxymethylfurfurylamine (HMFA) based on the HMF used.

EXAMPLE 3

Heterogeneously Catalytic Process Using Cu—Ni—Al Oxide Catalyst

To a 30 mL autoclave containing 0.5 mmol HMF, 80 mg CuNiAl oxide catalyst of Example 1 was introduced with 3 mL dioxane. The autoclave was then purged with 3×5 bar hydrogen and the pressure was maintained at 1 bar finally. And then 0.8 g ammonia was introduced into the reactor. The reaction mixture was stirred at room temperature for 4 hours and then heated to 150° C. and maintained for 16 hours. Characterization by gas chromatography indicated 51% yield of 2,5-bis(aminomethyl)furan (BAMF) and 24% yield of 5-hydroxymethylfurfurylamine (HMFA) based on the HMF used.

EXAMPLE 4

Heterogeneously Catalytic Process Using NiAl Oxide Catalyst

NiAl oxide catalyst was produced by the same way of Example 1. The molar ratio of Ni to Al was 6:1.

The operation of Example 2 was repeated except 73 mg NiAl oxide catalyst was used. Characterization of the reaction mixture by gas chromatography indicated 31% yield of 2,5-bis(aminomethyl)furan (BAMF) and 32% yield of 5-hydroxymethylfurfurylamine (HMFA) based on the HMF used.

EXAMPLE 5

Heterogeneously Catalytic Process Using Ni1404 Catalyst

The operation of Example 2 was repeated except 68 mg commercial catalyst Ni1404 from BASF was used. Characterization of the reaction mixture by gas chromatography indicated 33% yield of 2,5-bis(aminomethyl)furan (BAMF) and 35% yield of 5-hydroxymethylfurfurylamine (HMFA) based on the HMF used.

EXAMPLE 6

Heterogeneously Catalytic Process Using Ni5132 Catalyst

The operation of Example 2 was repeated except 95 mg commercial catalyst Ni5132 from BASF together with 20 g $Na_2CO_3$ was used. Characterization of the reaction mixture by gas chromatography indicated 30% yield of 2,5-bis(aminomethyl)furan (BAMF) and 24% yield of 5-hydroxymethylfurfurylamine (HMFA) based on the HMF used.

EXAMPLE 7

Preparation of Cu—Ni—Al Oxide Catalyst by Co-Precipitation Without Thermal Treatment The solution of precipitant (7.2 g $Na_2CO_3$ and 16.0 g NaOH, dissolved into 360 mL of deionized water) was added to the solution of metal nitrites (15.36 g $Cu(NO_3)_2 \cdot 3H_2O$, 4.92 g $Ni(NO_3)_2 \cdot 6H_2O$ and 23.0 g $Al(NO_3)_3 \cdot 9H_2O$, dissolved in 400 mL of deionized water) under stirring at 80° C. The obtained mixture was stirred for another 5 h, followed by washing with deionized water and drying at 100° C. for 15 hours.

The catalyst was pre-reduced before use —$H_2$ flow: 10-15 ml/min, heated from room temperature to 450° C., ramp: 10° C./min, and maintained at 450° C. for 3 hours and cooled down.

EXAMPLE 8

Heterogeneously Catalytic Process Using Cu—Ni—Al Oxide Catalyst

Three parallel tests are performed in the same way. To a 100 mL autoclave containing 0.65 mmol HMF, 70 mg CuNiAl oxide catalyst of Example 7, and 20 mg $Na_2CO_3$ was introduced with 8 mL dioxane. The autoclave was purged with 0.2 MPa hydrogen and the pressure was maintained at 1 bar finally. And then 3.5 g ammonia was introduced into the reactor. The reaction mixture was stirred at 90° C. for 6 hours and then at 180° C. for 60 hours.

The yield of 2,5-bis(aminomethyl)furan (BAMF) and 5-hydroxymethylfurfurylamine (HMFA) based on the HMF used (GC analysis) is shown in Table 1. It shows that the use of Cu—Ni—Al oxide catalyst by co-precipitation without calcination leads to high and stable BAMF yield.

TABLE 1

| Entry | Con./% | HMFA yield/% | BAMF yield/% | mass balance/% |
|---|---|---|---|---|
| 1 | 100 | 2.6 | 66.0 | 68.6 |
| 2 | 100 | 7.7 | 65.9 | 73.6 |
| 3 | 100 | 10.1 | 68 | 78.1 |

EXAMPLE 9

Heterogeneously Catalytic Process Using Cu—Ni—Al Oxide Catalyst

Three tests are performed by the same protocol. To a 100 mL autoclave containing 60 mg HMF, 70 mg CuNiAl oxide catalyst of Example 7, and 20 mg $Na_2CO_3$ was introduced with 50 mL dioxane. The autoclave was purged with 0.2 MPa hydrogen and the pressure was maintained at 1 bar finally. And then 3.5 g ammonia was introduced into the reactor. The reaction mixture was stirred at 90° C. for 6 hours and then at 190° C. for 60 hours.

The yield of 2,5-bis(aminomethyl)furan (BAMF) and 5-hydroxymethylfurfurylamine (HMFA) based on the HMF used (GC analysis) is shown in Table 2. It shows the use of Cu—Ni—Al oxide catalyst by co-precipitation without calcination leads to high and stable BAMF yield even the test scale is enlarged.

TABLE 2

| Entry | HMF/ mg | cat/ mg | $Na_2CO_3$/ mg | $H_2$/ MPa | $NH_3$/ g | Con./% | HMFA yield/% | BAMF yield/% | mass balance/% |
|---|---|---|---|---|---|---|---|---|---|
| 1 | 60 | 70 | 20 | 0.2 | 3.5 | 100 | 0.1 | 72.3 | 72.4 |
| 2 | 250 | 80 | 20 | 0.2 | 3.5 | 100 | 4.8 | 72.7 | 77.8 |
| 3 | 10500 | 2500 | 915 | 4.0 | 20 | 100 | 24.6 | 69.4 | 94.0 |

The invention claimed is:

1. A process for the production of an aromatic compound comprising at least two amine functions, the process comprising reacting:

A first reactant being an aromatic compound having at least one hydroxyl function and at least one aldehyde function, with A second reactant being a compound of formula (I),

R—$NH_2$      (I)

wherein R is H or an alkyl, alkenyl, aryl, cycloalkyl or heterocyclic group, in the presence of a catalyst and a reductant agent, wherein the catalyst comprises at least one metal element selected from the group consisting of nickel, cobalt, copper, tin, aluminum and chromium in elemental form and/or at least one metal oxide selected from the group consisting of $NiAlO_c$, $CuNiO_c$, $CuNiAlO_c$, $CuNiMgO_c$, $RuCuNiAlO_c$, $CuNiZnO_c$, $PtNiZnO_c$, and $CuZrO_c$, wherein c is greater than zero and less than a number sufficient to satisfy the valence requirements of the other elements present when in a fully oxidized state.

2. The process according to claim 1, wherein the first reactant is selected from the group consisting of: 5-hydroxymethyl furfural (HMF), 5-(3-(hydroxymethyl)phenyl)furfural, 5-(4-(hydroxymethyl)phenyl)furfural, 4-(hydroxymethyl)benzaldehyde, 3-(hydroxymethyl)benzaldehyde, 5-formyl-2-(hydroxymethyl)benzonitrile, 3-(5-(hydroxymethyl)furan-2-yl)acrylaldehyde and 5-(hydroxymethyl)thiophene-2-carbaldehyde.

3. The process according to claim 1, wherein the first reactant is selected from the group consisting of: 5-hydroxymethyl furfural (HMF), 3-(hydroxymethyl)benzaldehyde and 5-formyl-2-(hydroxymethyl)benzonitrile.

4. The process according to claim 1, wherein the second reactant is selected from the group consisting of: ammonia, methylamine, n-heptylamine, allylamine, benzylamine, 3-phenylprop-2-enylamine, cyclohexanamine, and (tetrahydrofuran-2-yl)methanamine.

5. The process according to claim 1, wherein the molar ratio of second reactant to first reactant is comprised from 10:1 to 150:1.

6. The process according to claim 1, wherein the reductant agent is hydrogen or a secondary alcohol.

7. The process according to claim 1, wherein molar ratio of the reductant agent to the first reactant is comprised from 1:1 to 10:1.

8. The process according to claim 1, wherein the catalyst comprises a support.

9. The process according to claim 8, wherein weight ratio of metal element is comprised from 0.5 wt % to 80 wt % based on total weight of catalyst.

10. The process according to claim 1, wherein the catalyst is Raney catalyst selected from a group consisting of Raney nickel, Raney cobalt and Raney copper.

11. The process according to claim 1, wherein weight ratio of catalyst to first reactant is comprised from 1:20 to 2:1.

12. The process according to claim 1, wherein the reaction medium is heated to desired temperature by Gradient Temperature-elevating Method.

13. The process according to claim 1, wherein the reaction is carried out in the presence of an inert atmosphere.

14. The process according to claim 1, wherein the method for preparing the catalyst comprising at least one metal oxide selected from the group consisting of $NiAlO_c$, $CuNiO_c$, $CuNiAlO_c$, $CuNiMgO_c$, $RuCuNiAlO_c$, $CuNiZnO_c$, $PtNiZnO_c$, and $CuZrO_c$ comprises the following steps:
  (i) preparing a mixture comprising the metal elements of the catalyst in ionic form;
  (ii) adding a co-precipitating agent to the mixture to precipitate the metal elements of the catalyst, to obtain a slurry;
  (iii) filtering and drying the slurry, to obtain a catalyst precursor; and
  (iv) subjecting the catalyst precursor to reduction, to obtain the catalyst.

* * * * *